(12) United States Patent
Shimada (10) Patent No.: US 7,475,987 B2
(45) Date of Patent: Jan. 13, 2009

(54) PERIMETER

(75) Inventor: Satoshi Shimada, Shizuoka-Ken (JP)

(73) Assignee: Kowa Company, Ltd. (JP)

( * ) Notice: Subject to any disclaimer, the term of this patent is extended or adjusted under 35 U.S.C. 154(b) by 0 days.

(21) Appl. No.: 11/516,369

(22) Filed: Sep. 6, 2006

(65) Prior Publication Data

US 2007/0177105 A1    Aug. 2, 2007

(30) Foreign Application Priority Data

Jan. 27, 2006    (JP) .............................. 2006-018782

(51) Int. Cl.
  *A61B 3/02*    (2006.01)
(52) U.S. Cl. ...................... 351/224; 351/243
(58) Field of Classification Search ......... 351/222–224, 351/237, 243
   See application file for complete search history.

(56) References Cited

U.S. PATENT DOCUMENTS 4,971,434 A * 11/1990 Ball ........................ 351/224
5,108,170 A * 4/1992 Sugiyama ................ 351/226
5,463,431 A * 10/1995 Suzuki et al. ............ 351/226
5,717,481 A * 2/1998 Obata et al. ............. 351/224
2005/0280776 A1* 12/2005 Suzuki ...................... 351/224

FOREIGN PATENT DOCUMENTS

JP      02-004307       1/1990
JP      2002-272685     9/2002

* cited by examiner

*Primary Examiner*—Scott J Sugarman
*Assistant Examiner*—Dawayne A Pinkney
(74) *Attorney, Agent, or Firm*—Robert F. Zielinski; Brian L. Belles; Buchanan Ingersoll & Rooney PC (57) ABSTRACT

It is easy to perceive a stimulus in a central portion of a visual field rather than in a peripheral portion thereof, and it is easy to perceive the stimulus for a younger examinee rather than for an older examinee even if the stimulus having the same luminance is indicated. In the perimeter according to the invention, the stimuli are indicated at various positions of a visual field dome, and the luminance of the stimulus is gradually raised before obtaining a response from an examinee through an operation switch. A value of the luminance of the indicated stimulus is set according to the position of the indicated stimulus and an age of the examinee, and the measurement accuracy is correct, thereby.

4 Claims, 10 Drawing Sheets

PERIMETER

This application claims benefit of priority to Japanese Patent Application No. 2006-18782 filed on Jan. 27, 2006.

BACKGROUND OF THE INVENTION

This invention relates to a perimeter for perimetry for an examinee.

BACKGROUND ART

When suffering from an ophthalmic disease, such as glaucoma and hemianopsia, it is known that a person has a visual field contraction or a visual field defect. For these reasons, perimeters having various structures have been proposed as devices for finding such diseases (see Japanese patent application the publication number of which is 2002-272685).

Figure 9:
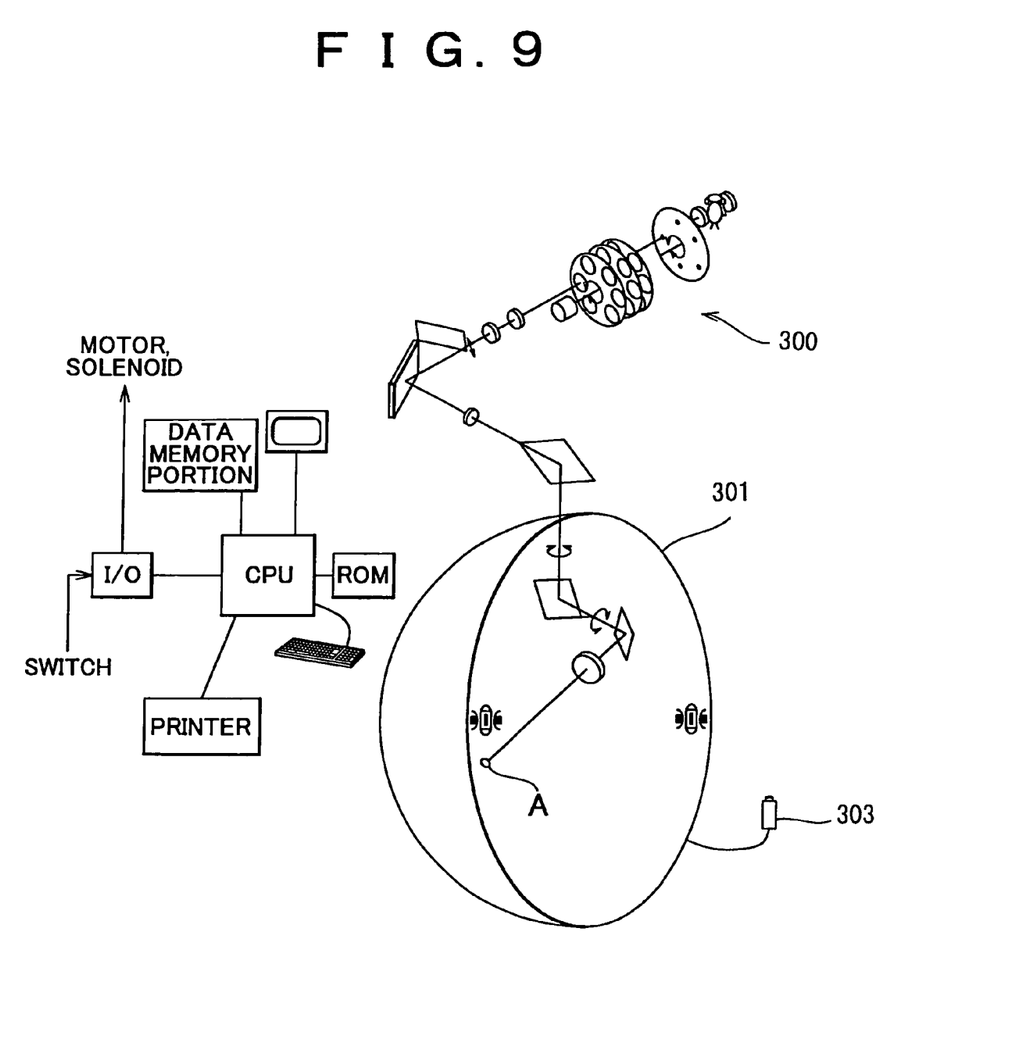
FIG. 9 is a typical view showing an instance of a structure of a conventional perimeter.

FIG. 9 is a typical view showing a structure of a conventional perimeter. In FIG. 9, a reference numeral 300 denotes a projection optical system for projecting stimuli D, and a reference numeral 301 denotes a visual field dome in the shape of a semi-sphere for projecting stimuli thereon. And, a reference numeral 303 denotes a response switch to be operated by an examinee.

When starting the perimeter in such a state that an examinee fixates a fixation target inside the visual field dome 301, the projection optical system 300 successively displays stimuli D at various positions of the visual field dome 301. An examinee operates the response switch 303 when perceiving the stimulus D, but does not operate when not perceiving. The visual field of an examinee can be measured from displayed positions of the stimuli D.

Japanese patent No. 2652227 discloses such a technique that if no response is received from an examinee when presenting the stimulus, the luminance of the stimulus to be indicated is raised without changing the indicated position of the stimulus, and a response from the examinee is waited again. In the case of the perimeter for indicating three stages of the luminances of the stimulus, a sensitivity of an examinee in each measurement point is classified into the following four stages.

(1) the stage wherein a response "I can see" is received from an examinee when watching the darkest stimulus which is firstly presented
(2) the stage wherein no response (1) is received from an examinee and the response "I can see" is received from an examinee when watching the slightly brighter stimulus which is next presented
(3) the stage wherein no response (2) is received from an examinee and the response "I can see" is received from an examinee when watching the further brighter stimulus which is next presented
(4) the stage wherein no response (1), (2) or (3) is received from an examinee since an examinee can not perceive any stimulus.

Figure 10:
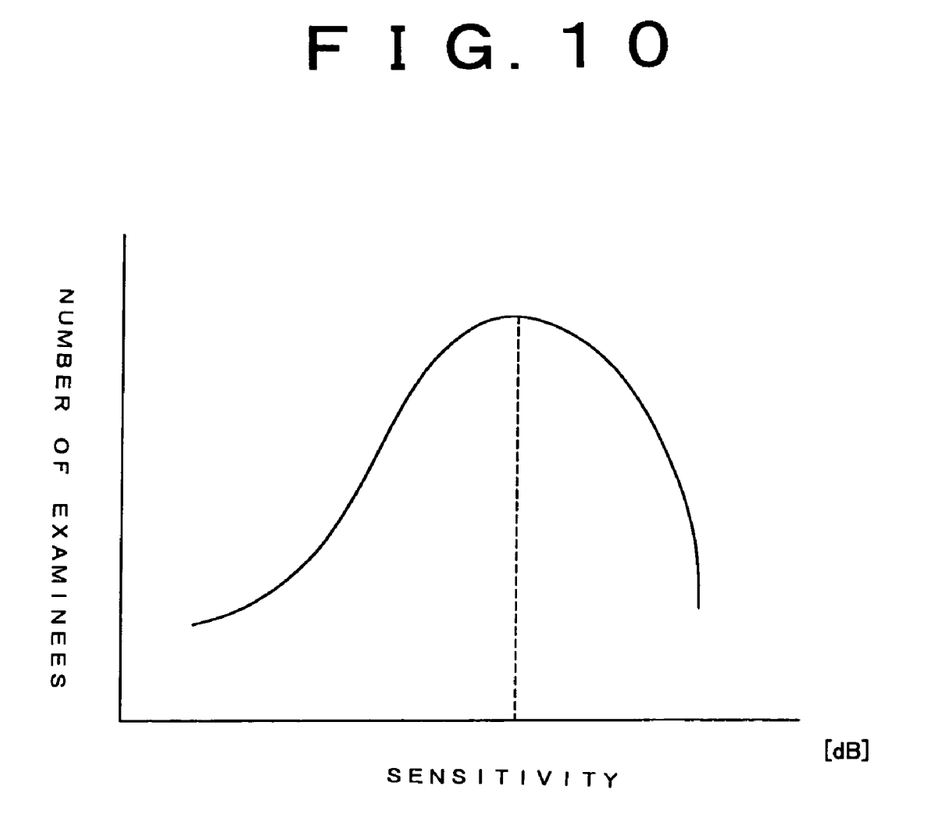
FIG. 10 is a typical view showing an instance of the shape of the normal sensitivity distribution curve in a position where a stimulus is indicated.

The above-mentioned luminances to be indicated are determined on the basis of the values for a person having normal healthy eyes. Concretely speaking, a specific curve as shown in FIG. 10 (refereed to as "the normal sensitivity curve" in the specification hereinafter) is prepared in such a manner that a test as to whether or not the examinees can perceive the stimuli having various luminances which are successively indicated at a specific position is conducted on examinees having normal healthy eyes, and a statistics between the luminance of the stimulus and a number of persons who can perceive the stimulus is obtained for many examinees having normal healthy eyes. Then, this normal sensitivity curve is regarded as a normal distribution, and the luminance having a peak value is determined as a normal value (the standard luminance). For instance, the first luminance is "the normal value −5"dB, the second luminance is "the normal value −10"dB, and the third luminance is 0 dB in order to gradually raise the luminance to be indicated.

But, such a problem that no correct test result is obtained remains since a fact that the above-mentioned normal sensitivity curves and the deviations (such as a value 5 dB or 10 dB) are different from each other every position of the stimulus to be indicated every year of the examinee is not considered in a conventional test.

Then, the object of the invention is to provide a perimeter for more correctively detecting a visual field angle.

SUMMARY OF THE INVENTION

One aspect of the invention is a perimeter for visual field contraction by successively presenting stimuli at various positions in said visual field, comprising:

a stimulus presentation unit for presenting said stimuli while gradually changing a luminance, said stimulus presentation unit having indicated position regulating means for regulating a position of said stimulus to be indicated, and indicated luminance regulating means for regulating said luminance of said stimulus to be indicated;

operation means for inputting whether or not an examinee can perceive said stimulus; and said indicated luminance regulating means having a standard luminance storing portion for storing a standard luminance every position of said stimulus to be indicated, a deviation storing portion for storing a deviation every position of said stimulus to be indicated, and a luminance control portion for gradually changing said luminance of said stimulus to be indicated on the basis of standard luminance data from said standard luminance storing portion and deviation data from said deviation storing portion.

According to this aspect of the invention, the visual field can be measured with the luminance of the stimulus according to the position where the stimulus is indicated, and the measured result is more correct, thereby.

Another aspect of the invention is the perimeter, wherein said deviation storing portion stores at least a first deviation for computing a first luminance to be indicated and a second deviation for computing a second luminance to be indicated.

According to this aspect of the invention, the visual field can be measured with the luminance of the stimulus according to the position where the stimulus is indicated, and the measured result is more correct, thereby.

Another aspect of the invention is the perimeter, wherein said standard luminance storing portion stores said standard luminance every position of said stimulus to be indicated every age of said examinee, and said deviation storing portion stores said deviations every position of said stimulus to be indicated every age of said examinee.

According to this aspect of the invention, the visual field can be measured with the luminance of the stimulus according to the position where the stimulus is indicated and the age of the examinee, and the measured result is more correct, thereby.

Another aspect of the invention is the perimeter, wherein said perimeter further comprising:

examinee data inputting means for inputting at least ages of said examinees; and a data reading portion for reading proper standard luminance and said deviation out of said standard luminance storing portion and said deviation storing portion on the basis of said age data from said examinee data input means and said data of said position where said stimulus is indicated, and for transmitting said read data to said luminance control portion.

According to this aspect of the invention, the visual field can be measured with the luminance of the stimulus according to the position where the stimulus is indicated and the age of the examinee, and the measured result is more correct, thereby.

Another aspect of the invention is the perimeter, wherein said perimeter further comprises a timer portion for starting to count time followed by a start of presentation of said stimulus or change of said luminance of said stimulus, and said luminance control portion can change said luminance of said stimulus on the basis of counting by said timer portion.

According to this aspect of the invention, the visual field can be measured with the luminance of the stimulus according to the position where the stimulus is indicated and the age of the examinee, and the measured result is more correct, thereby.

Another aspect of the invention is the perimeter, wherein said perimeter further comprises visual field judging means for judging said visual field of said examinee on the basis of a signal from said operation means, said indicated luminance data from said indicated luminance regulating means, and said indicated position data from said indicated position regulating means.

DESCRIPTION OF THE PREFERRED EMBODIMENTS

Figure 1:
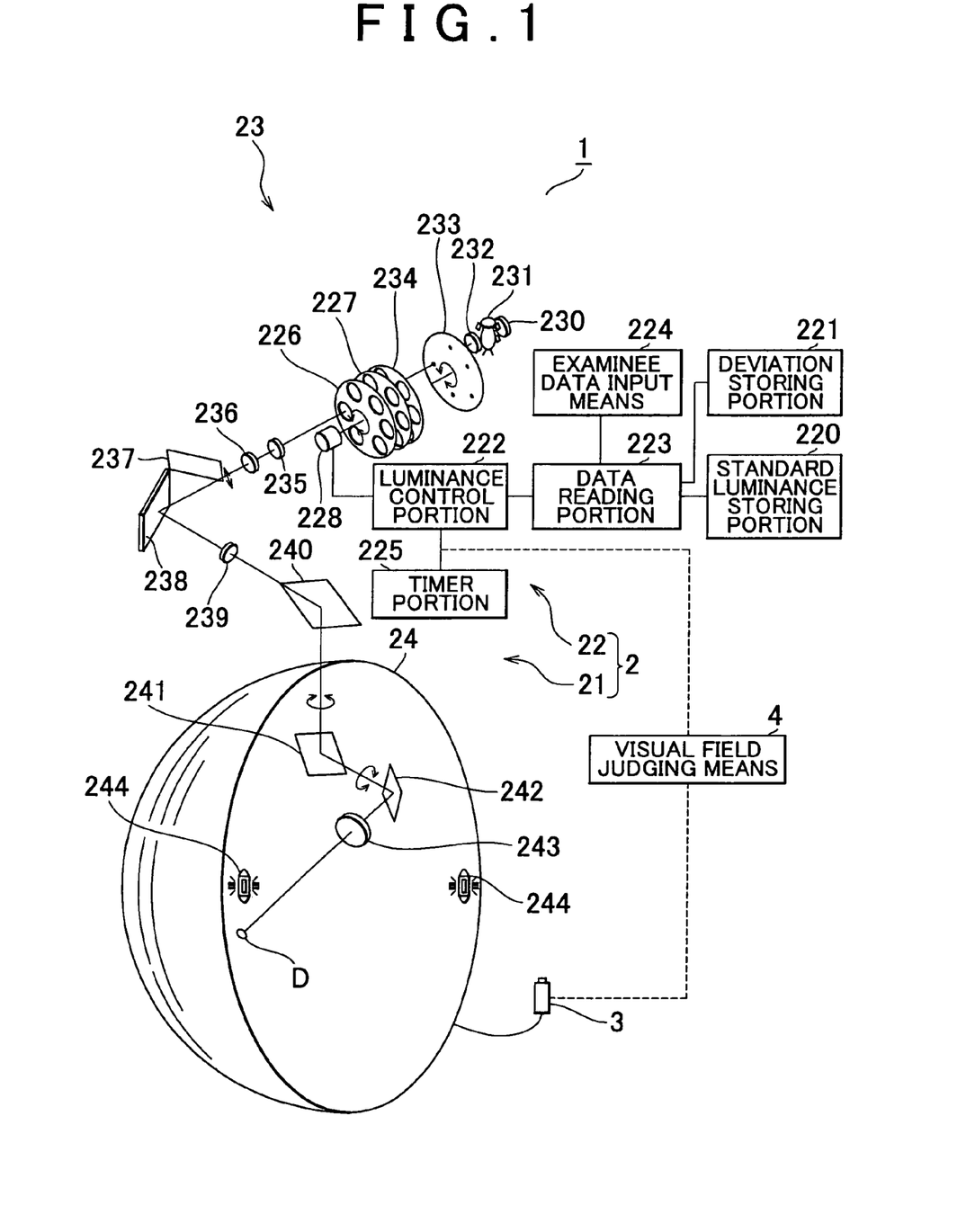
FIG. 1 is a typical view showing an instance of a structure of a perimeter according to the invention.
Figure 2:
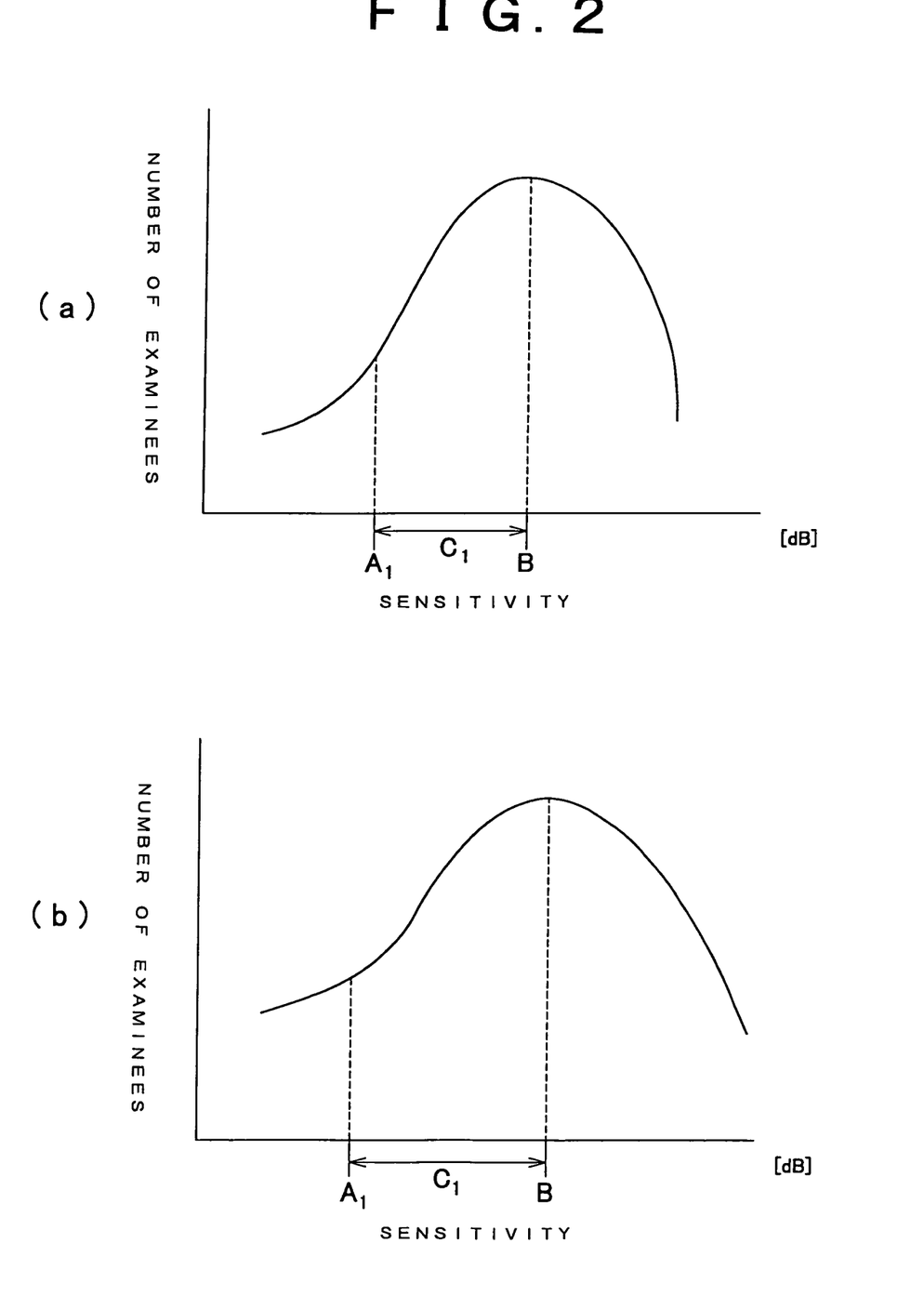
FIG. 2(a) is a typical view showing an instance of a shape of a normal sensitivity distribution curve in a position where a stimulus is indicated.
FIG. 2(b) is a typical view showing an instance of a shape of the normal sensitivity distribution curve in the other position where the stimulus is indicated.
Figure 3:
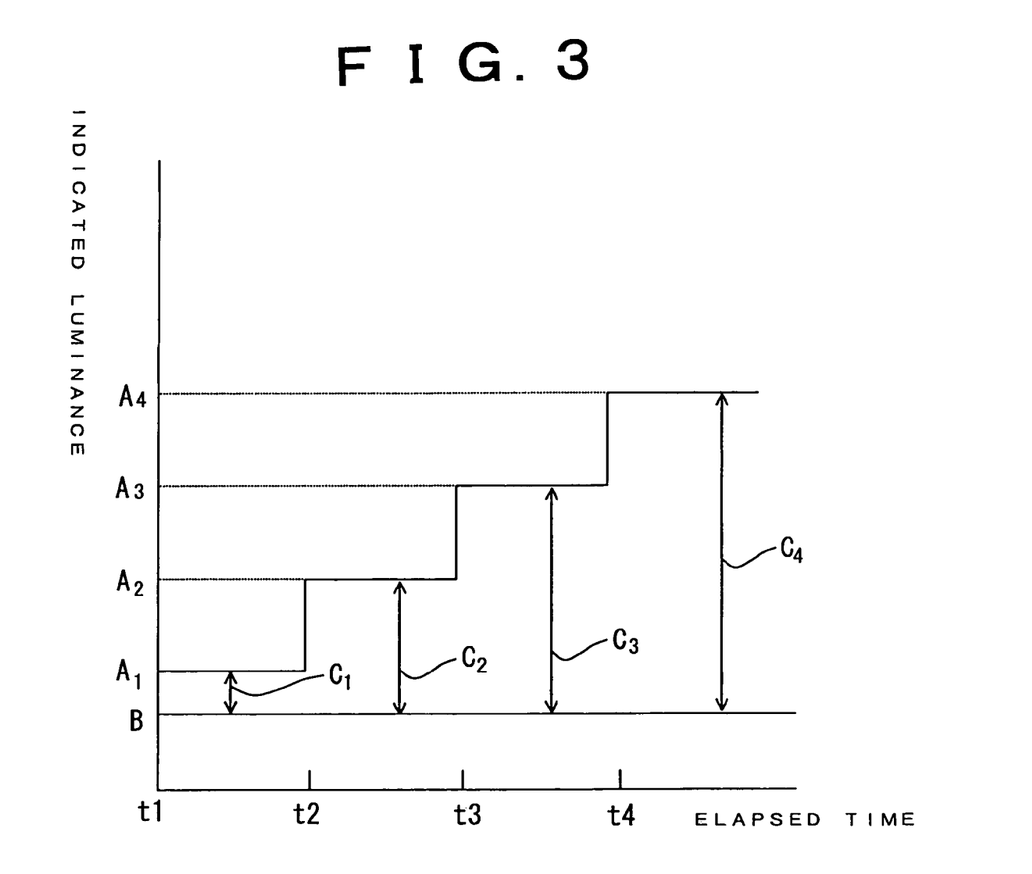
FIG. 3 is a typical view for explaining a change of a stimulus luminance in a position where the stimulus is indicated.
Figure 4:
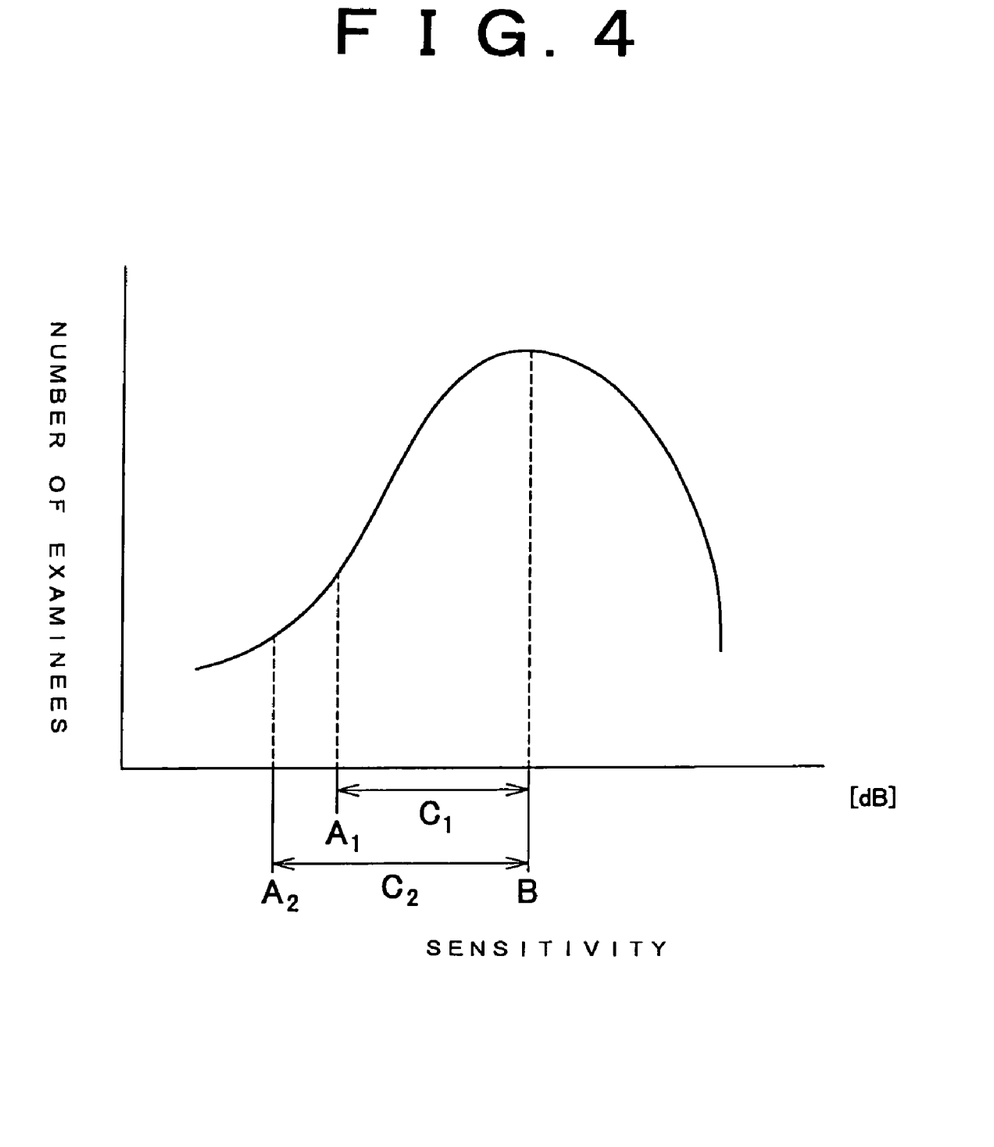
FIG. 4 is a typical view showing a relation between the change of the stimulus luminance in a position where the stimulus is indicated and the normal sensitivity distribution curve.
Figure 5:
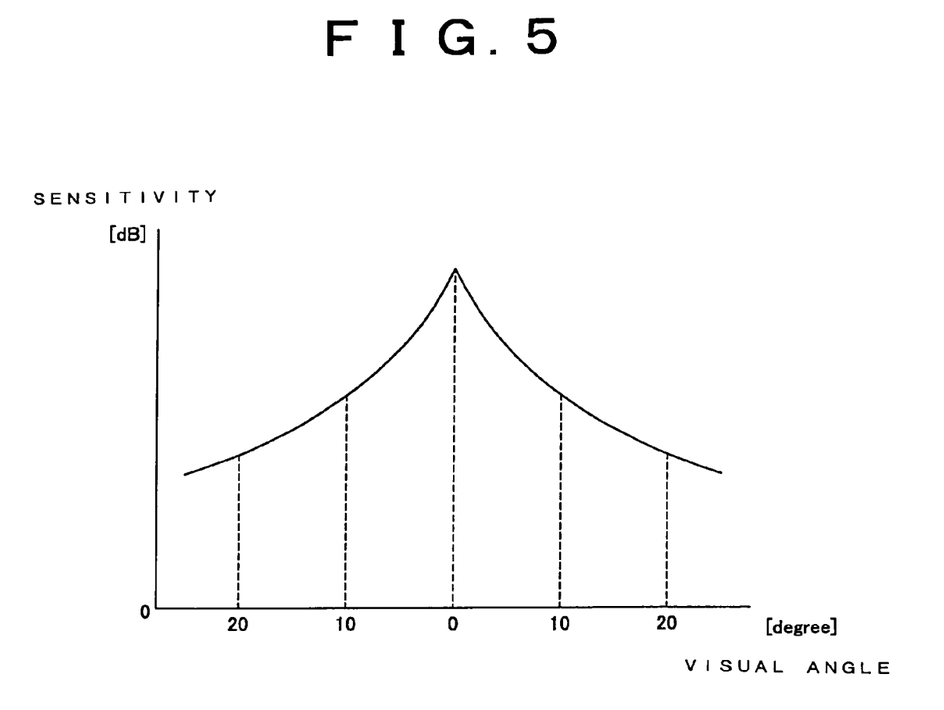
FIG. 5 is a view showing an instance of a characteristic curve which shows a relation between a visual angle and a sensitivity.
Figure 6:
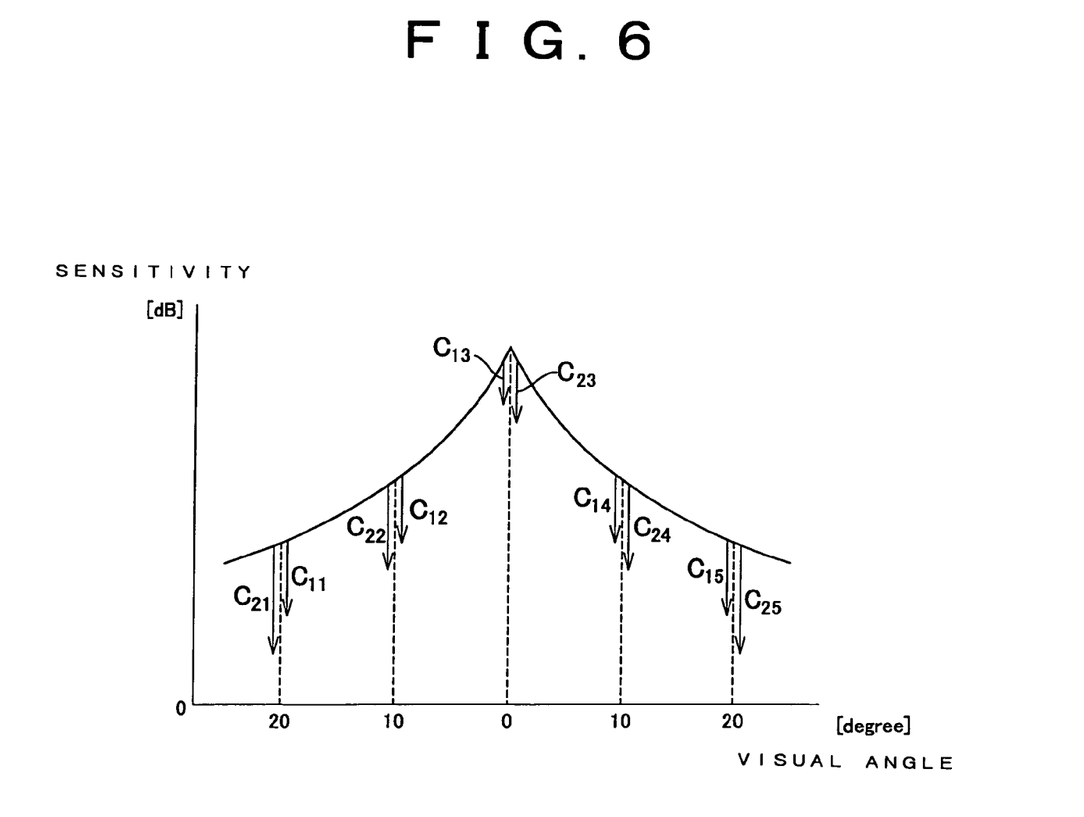
FIG. 6 is a view of the characteristic curve on which deviations are indicated.

A best mode for executing the invention is now explained hereinafter, referring to FIGS. 1 through 6. In the invention, FIG. 1 is a typical view showing an instance of a structure of a perimeter according to the invention, FIG. 2(a) is a typical view showing an instance of a shape of a normal sensitivity distribution curve (will be explained in detail hereinafter) in a position where a stimulus is indicated, FIG. 2(b) is a typical view showing an instance of a shape of the normal sensitivity distribution curve in the other position where the stimulus is indicated, FIG. 3 is a typical view for explaining a change of a stimulus luminance in a position where the stimulus is indicated, FIG. 4 is a typical view showing a relation between the change of the stimulus luminance in a position where the stimulus is indicated and the normal sensitivity distribution curve, FIG. 5 is a view showing an instance of a characteristic curve which shows a relation between a visual angle and a sensitivity, and FIG. 6 is a view of the characteristic curve on which deviations are indicated.

A perimeter according to the invention indicates the stimulus at various positions in a visual field in order so as to measure a visual field of an examinee by perception of the stimuli. The perimeter according to the invention denoted with reference number 1 for instance has a stimulus presentation unit 2 for presenting stimuli D, gradually changing luminance, and operation means 3 for inputting when an examinee can perceive the stimulus D. The stimulus presentation unit 2 has indicated position regulating means 21 for regulating a position of the indicated stimulus D, and indicated luminance regulating means 22 for regulating the luminance of the indicated stimulus D.

Preferably, the luminance of the stimuli D to be indicated is determined according to data obtained with a visual field measurement on healthy normal eyes in the invention. Such an aspect is now explained, hereinafter.

When executing a test for confirming with which luminance the stimulus D can be perceived in a process of gradually raising the luminance of the stimulus D on many examinees (having healthy normal eyes), a characteristic curve (referred to as "the normal sensitivity curve" hereinafter) as shown in FIG. 2(a) can be obtained. This normal sensitivity curve has a sensitivity for a horizontal axis and number of examinees (who can perceive the stimulus at the sensitivity) for a vertical axis. In the invention, this normal sensitivity curve is used as basic data, and the luminance of the stimulus to be indicated is determined on the basis of "a standard luminance" (which is a specific value in the curve). Although this normal sensitivity curve has a distribution having some degree of width in the right and the left with the peak as its center, this distribution is generated due to only personal errors of examinees. For this reason, this distribution does not always means that a peak portion is normal and the other portion is not normal. Then, the luminance of the peak portion or a specific luminance of the portion other than the peak portion maybe used as the standard luminance in the invention.

Since it is necessary to gradually raise the luminance of the stimulus to be indicated in the perimeter according to the invention, preferably, a numeric value, that is, a deviation is introduced and the following expressions may hold in the invention.

First luminance to be indicated $A_1$=standard luminance B−first deviation $C_1$ Second luminance to be indicated $A_2$=standard luminance B−second deviation $C_2$ Third luminance to be indicated $A_3$=standard luminance B−third deviation $C_3$ Fourth luminance to be indicated $A_4$=standard luminance B−fourth deviation $C_4$.

Preferably, the luminance of the stimulus to be indicated may be raised as follows.

present a stimulus at a first position at a first luminance to be indicated $A_1$
stop presentation of a stimulus
present a stimulus at a second position at the first luminance to be indicated $A_1$
stop presentation of a stimulus
present a stimulus at a third position at the first luminance to be indicated $A_1$
present a stimulus at the first position at a second luminance to be indicated $A_2$
stop presentation of a stimulus
present a stimulus at the second position at the second luminance to be indicated $A_2$
stop presentation of a stimulus
present a stimulus at the third position at the second luminance to be indicated $A_2$.

If an examinee can perceive the stimulus of the luminance to be indicated $A_1$ at the third position, it is possible to omit presentation of the luminance of the stimulus to be indicated $A_2$ at the third position. And, a time for presenting the stimulus and a time for stopping presentation of the stimulus may be freely adjusted. Furthermore, the luminance to be indicated may be changed, keeping the position to be indicated constant, as shown in FIG. 3 without changing the position to be indicated with a constant luminance to be indicated. In the figure, the luminance to be indicated is changed in four stages, but may be changed in two, three, five or more stages. A relation as shown in FIG. 3 (the relation among the standard luminance and the deviation and the luminance to be indicated) is shown as shown in FIG. 4 with the normal distribution curve. The reference number B in FIG. 4 denotes the standard luminance, the reference number $C_1$ denotes the first deviation, the reference number $A_1$ denotes the first luminance to be indicated, the reference number $C_2$ denotes the second deviation, and the reference number $A_2$ denotes the second luminance to be indicated.

FIG. 5 is a view which shows an instance of a specific curve showing the relation between a visual angle and a sensitivity. One perceives even the stimulus of relatively low luminance at a central portion of the visual field (that is, the portion where the visual angle is zero) where the sensitivity is higher, but one is prone to perceive only the luminance of the high luminance at a peripheral portion of the visual field (such as the portion where the visual angle is 10 or 20 degree).

This inclination can be seen in the person having normal eyes. For this reason, the above-mentioned normal sensitivity curve has a different shape every position of the stimulus to be indicated. For instance, some position of the stimulus to be indicated may have the shape as shown in FIG. 2(*a*) and another position of the stimulus to be indicated may have the shape as shown in FIG. 2(*b*). For this reason, a value of the standard luminance should be a different value every position of the stimulus to be indicated. Then, it is necessary to obtain the normal sensitivity curve every position of the stimulus to be indicated in order to determine the standard luminance every position of the stimulus to be indicated. Moreover, it is necessary to provide the indicated luminance regulating means 22 with a standard luminance storing portion (see a reference number 220 of FIG. 1) for storing the standard luminance every position of the stimulus to be indicated (that is, the standard luminance which is different every position of the stimulus to be indicated).

The standard luminance should be different according to the position of the stimulus to be indicated. This is also applied to the deviation. In other words, for instance, an examinee having normal healthy eyes can perceive the luminance "standard luminance $B_1$-3 dB at the position of the indicated stimulus" at some position of the indicated stimulus, but can not perceive the luminance "standard luminance $B_2$-3 dB at the position of the indicated stimulus" at another position of the indicated stimulus in an actual presentation of the stimulus to the examinee. That is, it is not sufficient to merely change the standard luminance "from $B_1$ into $B_2$" according to the position of the stimulus to be indicated, but it is necessary to change the value of the deviation, also. A p value (random variable) is an important value when changing the deviation every position of the stimulus to be indicated. This p value is a value which is statistically computed from data base of the visual field test for persons having normal healthy eyes. For instance, "P value 5 percent" means that "95 percent (100-p value) of examinees can perceive the luminance of the stimulus at the position of the stimulus to be indicated". That is, the examinees who can perceive the stimulus are always included in 95 percent of all examinees although the value of the deviation wherein "the p value is 5 percent" may be 3 dB at some position of the stimulus to be indicated or may be 4 dB at another position of the stimulus to be indicated. Then, the deviation of each position of the stimulus to be indicated is designated by the p value in the invention. And, it is necessary to change the deviation at the same position of the stimulus to be indicated, as shown in FIG. 3. For instance, change is executed in such a manner that "the p value for presenting the first stimulus is 5 percent", "the p value for presenting the second stimulus is 2 percent" and "the p value for presenting the third stimulus is 1 percent". By doing so, all of the first deviation, the second deviation, . . . is determined every position of the stimulus to be indicated. How to determine the p value may be freely set by an examiner according to a condition of the examinees.

FIG. 6 is a view showing an instance of the characteristic curve which shows a relation between the visual angle and the sensitivity, similar to FIG. 5. In the figure, reference numerals $C_{11}$, $C_{12}$, $C_{13}$, $C_{14}$ and $C_{15}$ denote the first deviation in the respective positions of the indicated stimuli, and reference numerals $C_{21}$, $C_{22}$, $C_{23}$, $C_{24}$ and $C_{25}$ denote the second deviation of the respective positions in the indicated stimuli. In case of the invention, the following relation holds at the same position of the indicated stimulus.

$|C_{1j}|<|C_{2j}|$ where j=1, . . . , 5.

And, it is necessary to set the second luminance of the stimulus to be indicated brighter than the first luminance. Besides, it is necessary to set the luminance of the stimulus to be indicated higher with an approach to a peripheral portion of the visual field as shown in the following expression.

$|C_{i3}|<|C_{i2}|<|C_{i1}|$ where j=1, 2.

Then, it is necessary to provide the indicated luminance regulating means 22 with a deviation storing portion 220 so that the deviation storing portion 221 stores at least the first deviation $C_1$ for computing the first luminance to be indicated $A_1$ and the second deviation $C_2$ for computing the second luminance $A_2$ to be indicated every position of the stimulus to be indicted.

For such a control, it is preferable to provide the indicated luminance regulating means 22 with a luminance control portion (see a reference number 222 of FIG. 1) so as to gradually change the luminance of the stimulus to be indicated at each position to be indicated on the basis of the standard luminance data from the standard luminance storing portion 220 and the deviation data from the deviation storing portion 221. In such a case, a data reading portion (see a reference number 223 of FIG. 1) may read the data from the standard luminance storing portion 220 and the deviation storing portion 221.

The above-mentioned normal sensitivity curve, the standard luminance and the deviation also receives an influence from ages of the examinees in addition to the influence from the positions of the indicated stimuli D. Then, preferably, the standard luminance storing portion 220 and the deviation storing portion 221 store the data according to the ages of the examinees (that is, the standard luminance and the deviation every each position of the stimulus to be indicated, every age of the examinee) in addition to the positions of the stimuli D to be indicated. In order to do so, it is preferable to provide examinee data input means 224 for inputting at least ages of the examinees, and preferable that the data reading portion 223 reads proper standard luminance and the deviation out of the standard luminance storing portion 220 or the deviation storing portion 221 on the basis of the data of the position where the stimulus D is indicated and the age data from the examinee data input means 224, and transmits the read data to the luminance control portion 222.

If the luminance control portion 222 controls the luminance as shown in FIG. 3, it is necessary to gradually raise the luminance of the stimulus D before receiving a response from an examinee. Then, a timer portion 225 for starting to count time followed by a start of the presentation of the stimulus D or the change of the luminance of the stimulus D may be provided so that the luminance control portion 222 can change the luminance of the stimulus D to be indicated on the basis of the counting by the timer portion 225.

And, it is preferable to provide visual field judging means 4 for judging the visual field of an examinee on the basis of the signal from the operation means 3, the indicated luminance data from the indicated luminance regulating means 22, and the indicated position data from the indicated position regulating means 21.

According to the invention, the visual field test can be executed with the luminance of the stimulus suitable for the position of the stimulus to be indicated or ages of the examinees, and the measurement result is correct, thereby.

The stimulus presentation unit 2 as shown in FIG. 1 has a projection optical system 23 for projecting the stimuli D, and a projection member 24 on which the stimuli D are projected by the projection optical system 23. But, the stimulus presentation unit 2 may have any structure as long as the stimuli can be presented in the visual field of an examinee. For instance, two or more LEDs may be located and are selectively lightened. Besides, the projection member 24 may have any shape, such as the shape having a curved surface and the shape having a plane although it has semi-sphere dome shape in FIG. 1.

If the stimulus presentation unit 2 has the projection optical system 23 and the projection member 24, it is preferable to provide the indicated luminance regulating means 22 with turrets 226, 227 rotatably supported, each having two or more filters having different attenunances, and a driving motor 228 for changing positions of the turrets 226, 227.

If the stimulus presentation unit 2 has the projection optical system 23 and the projection member 24, the indicated position regulating means 21 may be comprised of driving means (not shown) for changing positions of the structural elements of the projection optical system 23 (such as projector mirrors denoted with reference numbers 241, 242). Besides, if the stimulus presentation unit 2 is comprised of two or more LEDs, which LED should be lightened maybe controlled by the indicated position change portion. In both cases with the projection optical system and with the LEDs, change of the position to be indicated may be manually instructed by an examinee with a touch pen, a mouse or a keyboard, watching a display during the test, or may be automatically instructed with program prepared in advance.

Next, a method of measuring the visual field according to the invention is now mentioned.

When starting the perimeter 1 according to the invention while an examinee is fixating a specific fixation target, the stimulus presentation unit 2 presents the stimulus D at a predetermined luminance at a predetermined position in the visual field of the examinee. The luminance of the stimulus D is determined on the basis of the standard luminance data from the standard luminance storing portion 220 and the deviation data of the deviation storing portion 221. The stimuli D are presented at various positions with various luminances in order, and the visual field judging means 4 judges the visual field of the examinee on the basis of the indicated luminance data from the indicated luminance regulating means 22 and indicated position data from the indicated position regulating means 21 when the operation means 3 being operated.

Figure 7:
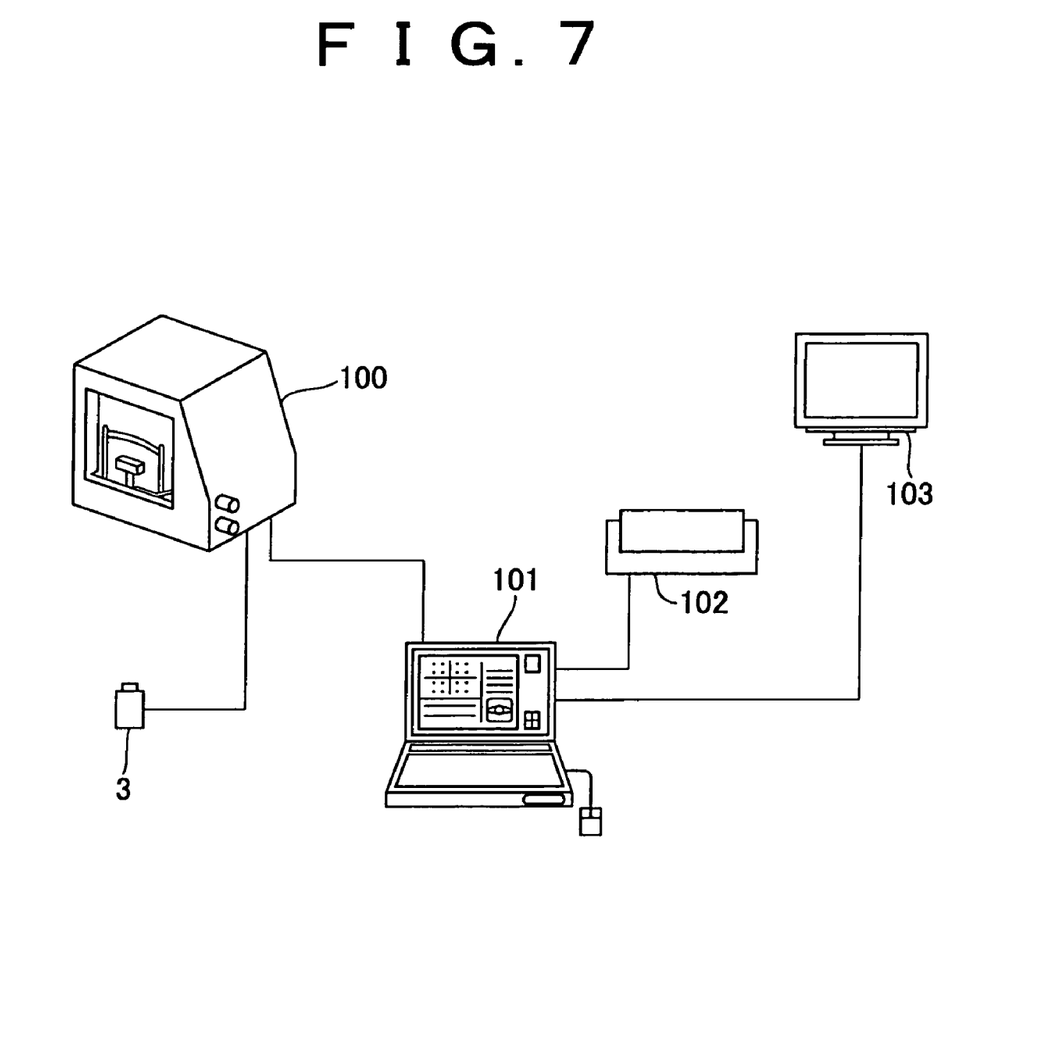
FIG. 7 is a typical view showing a structure of a visual field measuring system according to an embodiment of the invention.

In this embodiment, a visual field measuring system as shown in FIG. 7 is formed. Concretely speaking, this system is comprised of a stimulus presentation portion 100 for presenting the stimulus D, a personal computer 101 for controlling the stimulus presentation portion 100, a printer 102, a monitor 103, and a response switch (operation means) 3 to be operated by an examinee when perceiving the stimulus D.

The personal computer 101 in which predetermined software is installed in advance has the above-mentioned standard luminance storing portion 220, the deviation storing portion 221, the data reading portion 223, the luminance control portion 222, the timer portion 225, and the visual field judging means 4. Besides, the personal computer 101 stores respective data of the standard luminance and the deviation. The above-mentioned p value and the ages of examinees can be inputted through this personal computer.

The stimulus presentation portion 100 has the projection optical system 23 for projecting the stimulus D, and the visual field dome (projection member) 24 for projecting the stimulus D in order to present the stimulus D in the visual field of the examinee.

As shown in FIG. 1, the projection optical system 23 is comprised of a stimulus projection lamp (halogen lamp) 231 which is a light source, a reflecting mirror 230 which is located at a rear side of the lamp 231, a condenser lens 232 for converging light which is located at a front side of the lamp 231, an aperture 233 (which is explained in detail hereinafter) for determining a shape and a size of the stimulus D, a color filter turret 234 (which is explained in detail hereinafter) for determining a color of the stimulus D, a relay lens 235, a focus lens 236, a shutter 237, a mirror 238, a relay lens 239, a mirror 240, projector mirrors 241, 242, and a projector lens 243. A reference number 244 denotes a background lighting lamp 244.

The aperture 233 having different sized holes can be moved in a rotational direction and in an optical axis direction so as to properly change the size of the stimulus D to be projected on the visual dome 24.

And, the color filter turret 234 has a filter for a rod A and a filter for a cone B, and can be rotated by a servo motor (not shown).

Two rotatable ND filter turrets 226, 227 are located on an optical path between the color filter turret 234 and the relay lens 235. Each of the ND filter turrets 226, 227 has two or more filters having different attenuances, so that the luminance of the stimulus can be adjusted in a unit of 1 dB by adjusting rotational positions of the respective ND filter turrets 226, 227 so as to change a combination of filters for transmitting light. In this embodiment, driving mechanism, such as the servo motor 228, is connected with the ND filter turrets 226, 227 so that the luminance can be adjusted by controlling driving of the driving mechanism with the luminance control portion 232.

Besides, a servo motor (not shown) is connected with the projector mirrors 241, 242 so that the position of the stimulus D to be indicated can be changed by changing the angles of the respective projector mirrors 241, 242 by controlling driving of the servo motor. In other words, the indicated position regulating means 21 is comprised of these projector mirrors 241, 242 and the servo motor in this embodiment.

Furthermore, the shutter 237 can be opened and closed with a solenoid (not shown), so that the stimulus D is presented in an open state, and no stimulus D is presented in a closed state.

And, a jaw stand (not shown) for putting a jaw of an examinee thereon is located at a position facing the visual field dome 24.

The perimeter 1 is provided with a response switch (operation means) 3 which an examinee can operates when perceiving the stimulus D.

Figure 8:
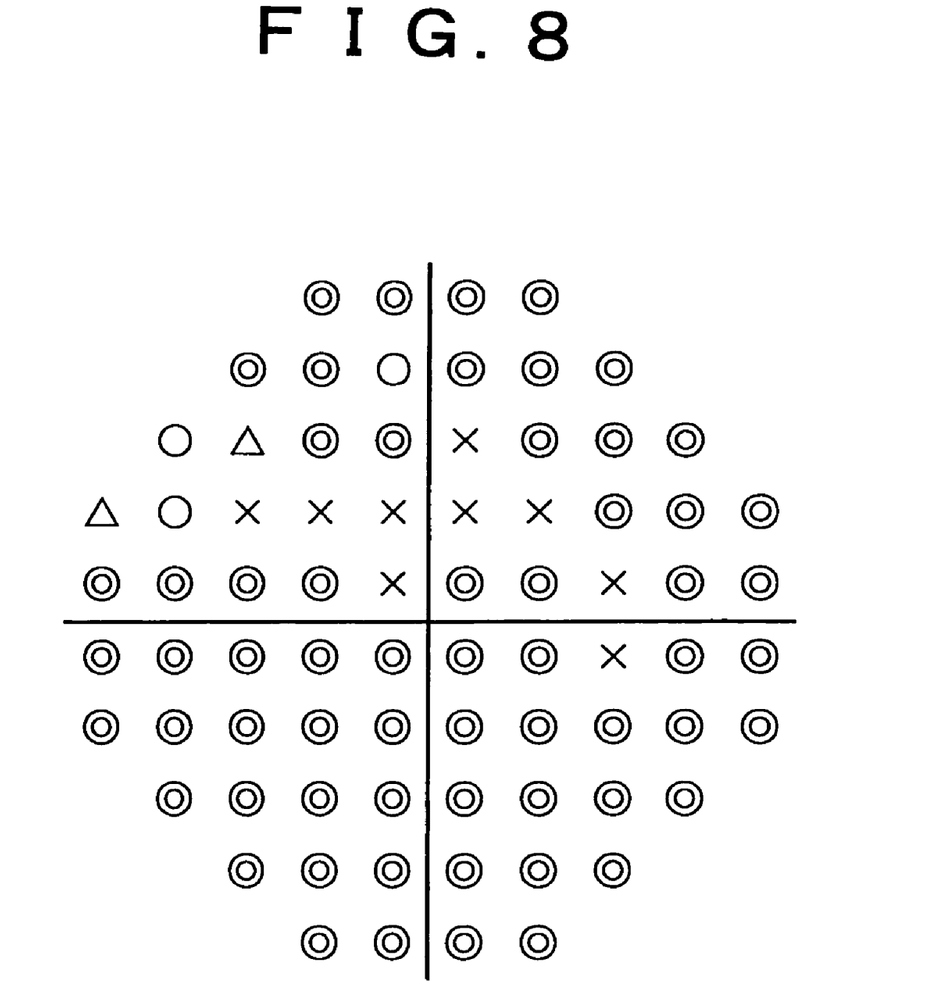
FIG. 8 is a view showing an instance of examination results.

FIG. 8 is a view showing an instance of examination results wherein ⊚ denotes a point of the stimulus which can be perceived at the first luminance to be indicated $A_1$, ○ denotes a point of the stimulus which can be perceived at the next luminance to be indicated $A_2$, Δ denotes a point of the stimulus which can be perceived at the third luminance to be indicated $A_3$, and X denotes a point of the stimulus which can not be perceived.

The present invention has been explained on the basis of the example embodiments discussed. Although some variations have been mentioned, the embodiments which are described in the specification are illustrative and not limiting. The scope of the invention is designated by the accompanying claims and is not restricted by the descriptions of the specific embodiments. Accordingly, all the transformations and changes within the scope of the claims are to be construed as included in the scope of the present invention.

The invention claimed is:

1. Perimeter for visual field contraction by successively presenting stimuli at various positions in said visual field, comprising:
    a stimulus presentation unit for presenting said stimuli while gradually changing a luminance, said stimulus presentation unit having indicated position regulating means for regulating a position of said stimulus to be indicated, and indicated luminance regulating means for regulating said luminance of said stimulus to be indicated;
    operation means for inputting whether or not an examinee can perceive said stimulus; and
    said indicated luminance regulating means having a standard luminance storing portion for storing a standard luminance at every position of said stimulus to be indicated, a deviation storing portion for storing a deviation at every position of said stimulus to be indicated, the deviation correlating to a p-value and said position of said stimulus, and a luminance control portion for gradually changing said luminance of said stimulus to be indicated on the basis of standard luminance data from said standard luminance storing portion and deviation data from said deviation storing portion, wherein said standard luminance storing portion stores said standard luminance every position of said stimulus to be indicated and every age of said examinee, and wherein said deviation storing portion stores said deviations, every position of said stimulus to be indicated and every age of said examinee; examinee data inputting means for inputting at least ages of said examinees; and a data reading portion for reading proper standard luminance and said deviation out of said standard luminance storing portion and said deviation storing portion on the basis of said age data from said examinee data input means and said data of said position where said stimulus is indicated, and for transmitting said read data to said luminance control portion.

2. The perimeter according to claim 1, wherein said deviation storing portion stores at least a first deviation for computing a first luminance to be indicated and a second deviation for computing a second luminance to be indicated.

3. The perimeter according to claim 1, wherein said perimeter further comprises a timer portion for starting to count time followed by a start of presentation of said stimulus or change of said luminance of said stimulus, and said luminance control portion can change said luminance of said stimulus on the basis of counting by said timer portion.

4. The perimeter according to claim 1, wherein said perimeter further comprises visual field judging means for judging said visual field of said examinee on the basis of a signal from said operation means, said indicated luminance data from said indicated luminance regulating means, and said indicated position data from said indicated position regulating means.

* * * * *